(12) United States Patent
Graney et al.

(10) Patent No.: US 8,057,217 B2
(45) Date of Patent: Nov. 15, 2011

(54) APPARATUS AND METHOD FOR INJECTION MOLDING AN INTRAOCULAR LENS DEVICE

(75) Inventors: Anita M. Graney, Rochester, NY (US); Graham W. Biddle, Ontario, NY (US); Thomas Lodadio, Rochester, NY (US); William J. Appleton, Rochester, NY (US)

(73) Assignee: Bausch + Lomb Incorporated, Rochester, NY (US)

( * ) Notice: Subject to any disclaimer, the term of this patent is extended or adjusted under 35 U.S.C. 154(b) by 2059 days.

(21) Appl. No.: 10/954,322

(22) Filed: Sep. 30, 2004

(65) Prior Publication Data

US 2006/0069431 A1 Mar. 30, 2006

(51) Int. Cl.
*B29D 11/00* (2006.01)
(52) U.S. Cl. .................... 425/588; 425/117; 425/808
(58) Field of Classification Search ............ 425/117, 425/188, 357, 468, 588, 808; 249/177; 264/2.7; 623/6.11, 6.38, 6.41, 6.46
See application file for complete search history.

(56) References Cited

U.S. PATENT DOCUMENTS

| | | | |
|---|---|---|---|
| 3,971,841 A | 7/1976 | Rubinstein | |
| 4,252,294 A | 2/1981 | Uchio | |
| 4,348,484 A * | 9/1982 | Joormann et al. | 501/45 |
| 4,560,342 A * | 12/1985 | Ishida et al. | 425/562 |
| 4,619,662 A * | 10/1986 | Juergens, Jr. | 623/6.18 |
| 4,836,960 A | 6/1989 | Spector et al. | |
| 5,143,659 A * | 9/1992 | Hamblen et al. | 264/1.1 |
| 5,275,623 A | 1/1994 | Sarfarazi | |
| 5,585,049 A * | 12/1996 | Grisoni et al. | 264/1.7 |
| 5,603,871 A * | 2/1997 | Koseko et al. | 264/1.9 |
| 5,645,665 A * | 7/1997 | Salazar et al. | 156/73.1 |
| 5,674,435 A * | 10/1997 | Blake | 264/2.7 |
| 5,762,836 A | 6/1998 | Bos et al. | |
| 5,770,119 A * | 6/1998 | Walker et al. | 264/1.37 |
| 5,904,746 A | 5/1999 | Okada | |
| 6,096,078 A | 8/2000 | McDonald | |
| 6,197,227 B1 * | 3/2001 | Appleton et al. | 264/1.1 |
| 6,210,610 B1 * | 4/2001 | Saito et al. | 264/2.2 |
| 6,423,094 B1 | 7/2002 | Sarfarazi | |
| 6,488,708 B2 | 12/2002 | Sarfarazi | |
| 6,499,986 B1 * | 12/2002 | Saito | 425/190 |
| 6,537,316 B1 | 3/2003 | Chambers | |
| 6,732,993 B2 * | 5/2004 | Dean | 249/117 |
| 6,769,900 B2 | 8/2004 | Murphy et al. | |
| 6,884,261 B2 * | 4/2005 | Zadno-Azizi et al. | 623/6.12 |
| 6,939,486 B2 | 9/2005 | DeRyke et al. | |
| 7,217,112 B2 * | 5/2007 | Kyburz et al. | 425/117 |
| 2001/0007513 A1 | 7/2001 | Koshimizu et al. | |

(Continued)

FOREIGN PATENT DOCUMENTS

EP    0875354 A1    11/1998

(Continued)

OTHER PUBLICATIONS

U.S. Appl. No. 10/445,762, filed May 27, 2003, Sarfarazi et al.

(Continued)

*Primary Examiner* — Dimple Bodawala
(74) *Attorney, Agent, or Firm* — Jeffrey B Powers

(57) ABSTRACT

Apparatus and methods for injection molding intraocular lenses includes an embodiment having first and second runners extending into first and second optic cavities of a mold configured to make a dual optic lens device.

30 Claims, 10 Drawing Sheets

U.S. PATENT DOCUMENTS

| | | | |
|---|---|---|---|
| 2002/0002404 A1 | 1/2002 | Sarfarazi | |
| 2002/0173847 A1 | 11/2002 | Pham et al. | |
| 2002/0185763 A1* | 12/2002 | Pegram et al. | 264/2.3 |
| 2003/0018384 A1 | 1/2003 | Valyunin et al. | |
| 2003/0234456 A1 | 12/2003 | DeRyke et al. | |
| 2004/0119177 A1* | 6/2004 | Reed et al. | 264/1.32 |
| 2005/0267575 A1* | 12/2005 | Nguyen et al. | 623/6.34 |
| 2006/0001186 A1* | 1/2006 | Richardson et al. | 264/2.7 |

FOREIGN PATENT DOCUMENTS

| | | |
|---|---|---|
| EP | 0 875 354 | 10/2002 |
| EP | 1633550 B1 * | 9/2004 |
| JP | 59-199227 | 11/1984 |
| JP | 01301217 A * | 12/1989 |
| JP | 2000-61967 | 2/2000 |
| WO | WO 97/26124 * | 7/1997 |
| WO | WO 02/071983 A1 * | 9/2002 |
| WO | WO 2004/010905 | 2/2004 |
| WO | WO 2004/010905 A2 | 2/2004 |
| WO | WO 04/106045 A1 * | 12/2004 |
| WO | WO 2006/039269 A2 * | 4/2006 |

OTHER PUBLICATIONS

U.S. Appl. No. 10/445,762, filed May 27, 2003, Kyburz, et al.
Engineering Materials Handbook, Desk Edition, Nov. 1995.
Opposition of EP 1 799 437 by Abbott Medical Optics, Inc., Oct. 4, 2010.
Guide for Injection Moulding of Silastic LSR, Dow Corning 1998.
Toensmeier, Another Option in Parts design: liquid injection molding silicones, Modern Plastics International, Jul. 1989.
Laghi, Commerical and technical developments of liquid injection molding of silicone elastomers, Rubber World, May 1988, pp. 17-18.

* cited by examiner

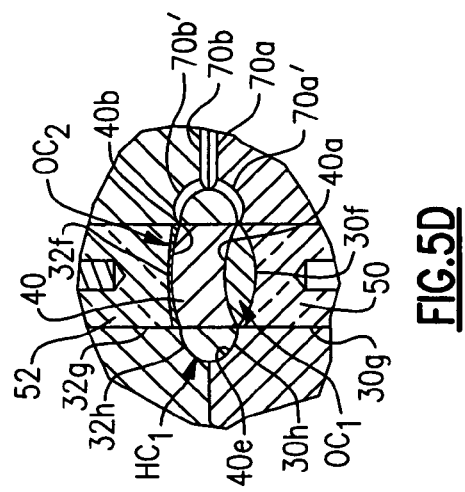
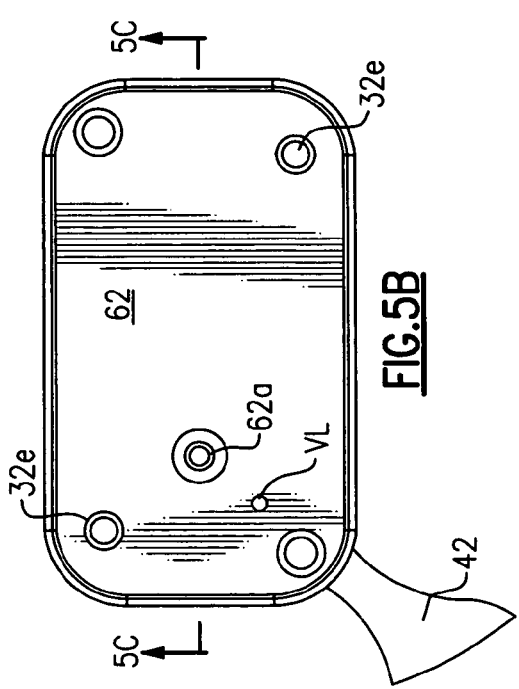
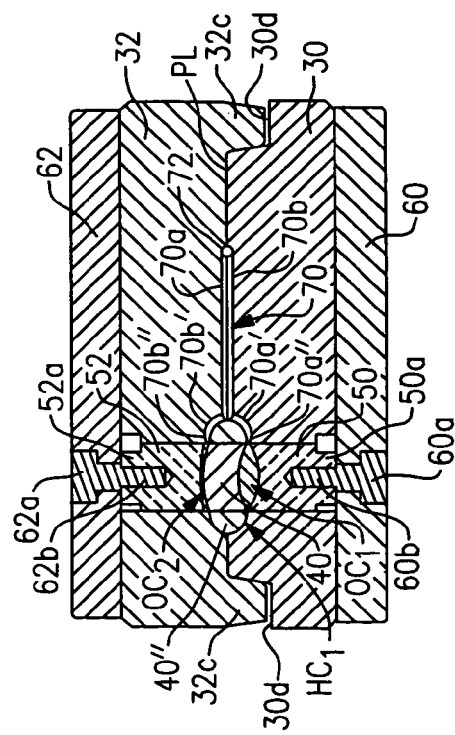

APPARATUS AND METHOD FOR INJECTION MOLDING AN INTRAOCULAR LENS DEVICE

BACKGROUND OF THE INVENTION

The present invention relates to injection molding and more particularly relates to novel apparatus and methods for liquid injection molding an intraocular lens ("IOL"). Intraocular lenses having a single optic have been known and used for many years. IOL manufacturing has included cast molding, lathing and liquid injection molding (LIM). In the LIM technique, a cold liquid lens material, for example a pre-mixed two-part liquid silicone, is injected into a heated mold cavity of the desired configuration and allowed to cure and harden. While LIM is a cost-effective technique for making intraocular lenses, improvements could be made to various aspects thereof such as, for example, surface finishes and gating designs that do not create unwanted knit lines, gate vestiges and the like.

More recently, accommodating intraocular lens devices having two optics interconnected by one or more haptics have been disclosed in the following U.S. patents and applications to Faezeh Sarfarazi, the entirety of which are incorporated herein by reference:

U.S. Pat. No. 5,275,623 "Elliptical Accommodative Intraocular Lens For Small Incision Surgery";

U.S. Pat. No. 6,423,094 "Accommodative Lens Formed From Sheet Material";

U.S. Pat. No. 6,488,708 "Open Chamber Elliptical Accommodative Intraocular Lens System";

U.S. Ser. No. 10/445,762 filed on May 27, 2003 entitled "Mold for Intraocular Lens".

The Sarfarazi accommodating lens device includes two optics, one negative and the other positive for placing in the evacuated lens capsule of an eye. The optics are interconnected along their peripheries by one or more haptics which space the optics from each other and assist in properly positioning the device in the eye. The haptics are formed from a flexible material such that they may flex in response to forces exerted by the eye's ciliary muscles which control accommodation. The haptics will thus flex and bow further radially outwardly upon a compressive force being applied to the device, whereby the two optics are drawn closer together to achieve an accommodative effect in the eye. When the ciliary muscles relax, the haptics flex in the opposite direction (toward a straightened position) causing the optics to space further apart and the lens device returns the eye to its natural, unaccommodative state.

As stated above, single optic intraocular lenses have been known and used for decades while the two lens accommodative intraocular lens device is new and not yet seen on the market. It will be appreciated that manufacturing, packaging and otherwise handling a two optic lens device presents issues not present in the manufacture, packaging and handling of single optic intraocular lenses. In the '762 application listed above, a two optic IOL is injection molded in a mold cavity having a removable metal insert centrally located between first and second cavity blocks. The IOL first optic is formed between the first cavity block and a first surface of the mold insert and the second optic is formed between the second cavity block and the opposite surface of the mold insert. The haptics interconnect and are integrally formed with the first and second optics. The inner surfaces of the haptics are formed by the perimeter of the mold insert and the outer surfaces thereof are formed by the first and second cavity blocks. Silicone is injected into the cavity and allowed to cure to form the IOL. The cavity blocks are opened and the mold insert is removed therefrom. The mold insert is preferably connected to a handle to permit easy handling thereof. The IOL remains connected to the mold insert as the mold insert is removed from between the cavity blocks. Since the IOL is made of silicone, it may be removed from the mold insert by carefully stretching it to allow the mold insert to pass between an opening defined between the haptic or haptics. The mold insert is then replaced between the cavity blocks to injection mold another IOL. The injection mold tools are made of suitable materials able to withstand repeated molding cycles.

While the above manufacturing method is satisfactory for injection molding a two optic IOL, improvements may be made. For example, a need exists for a robust liquid injection molding method which produces high quality IOLs. It would also be desirable to have a liquid injection molding apparatus and method that reduces or eliminates knit lines, gate vestiges and the like on the molded IOL such that post-molding processes to remove such molding remnants are likewise reduced or eliminated.

SUMMARY OF THE INVENTION

In one aspect, the present invention provides predetermined surface finishes on preselected mold cavity parts of a liquid injection molding apparatus. Surface finishes can be used for various purposes such as, for example, creating a "frosted" appearance to one or more haptics of an IOL which may improve visualization for the surgeon during the implantation procedure. Surface finishes may also be used to facilitate removal of the lens device from the mold insert, for example.

In another aspect, the invention provides a liquid injection molding apparatus and method for making IOLs which are of high quality and require a minimum of post molding operations such as edging to remove gate vestiges.

In yet another aspect, the invention comprises an improved apparatus and method for liquid injection molding a dual optic intraocular lens device such as lens device 10. In a preferred embodiment, injection of the liquid lens material into the mold cavity is provided through first and second gates leading into the first and second optic cavities, respectively, thereby improving the mold flow dynamics resulting in a higher quality lens device. In a preferred embodiment, the first and second gates taper to reduce or eliminate gate vestiges on the resultant lens device.

In another aspect, the present invention provides an improved mold insert for a liquid injection molding apparatus and method.

The present invention will be described with regard to preferred embodiments thereof, it being understood that modifications may be made without departing from the full scope of the invention as claimed. It is also noted that certain aspects of the invention may be solely applicable to a dual optic lens device while other aspects of the invention may be more broadly applicable to lens devices having one or more optics and with or without one or more haptics integrally molded therewith.

BRIEF DESCRIPTION OF THE DRAWINGS

FIG. 5B is a top plan view of FIG. 5A with the handle of the mold insert shown fragmented;

FIG. 5C is a cross-sectional view as taken generally along the line 5C-5C in FIGS. 5A and B;

FIG. 5D is an enlarged, fragmented view of the mold cavity seen in FIG. 5C;

DETAILED DESCRIPTION

The present invention will be described with regard to preferred embodiments thereof, it being understood that modifications may be made without departing from the full scope of the invention as claimed. It is also noted that certain aspects of the invention may be solely applicable to a dual optic lens device while other aspects of the invention may be more broadly applicable to lens devices having one or more optics with or without one or more haptics separately attached or integrally molded therewith.

Figure 1:
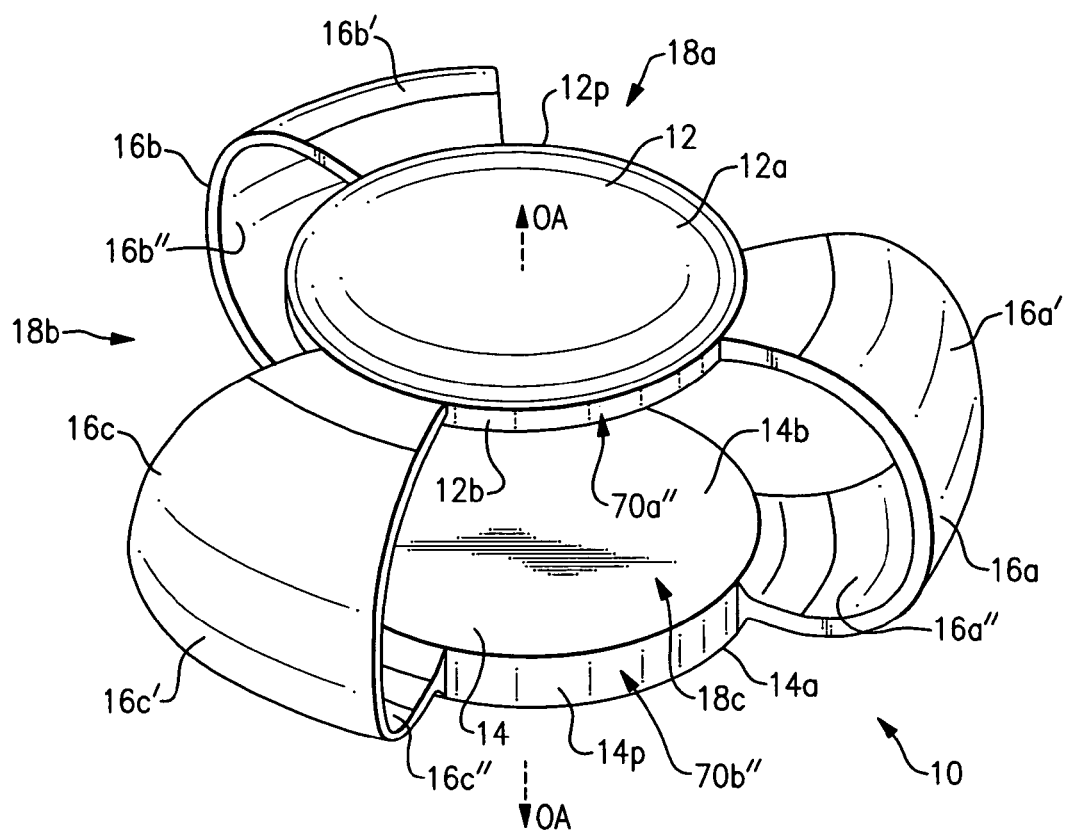
FIG. 1 is an enlarged, perspective view of an embodiment of a dual optic intraocular lens.
Figure 2:
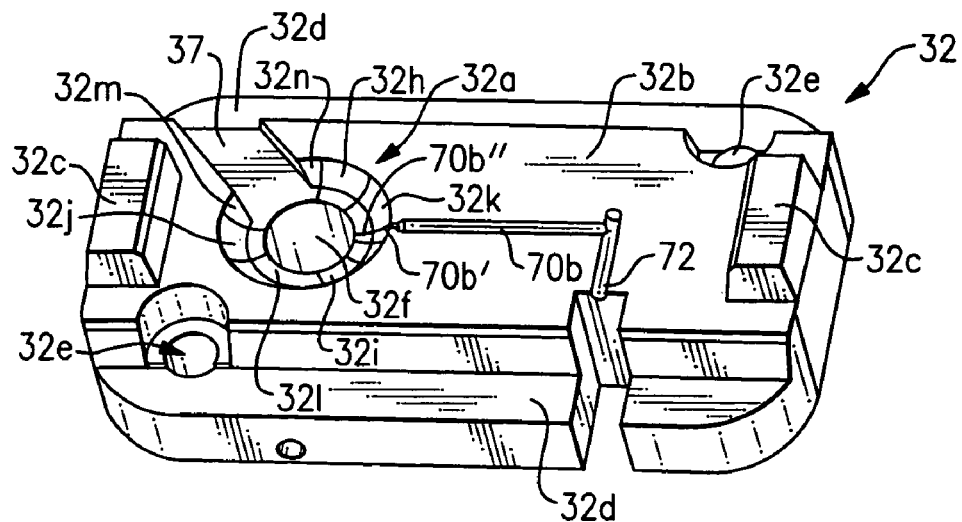
FIG. 2 is a perspective view of a first half of a cavity block according to an embodiment of the invention.
Figure 3:
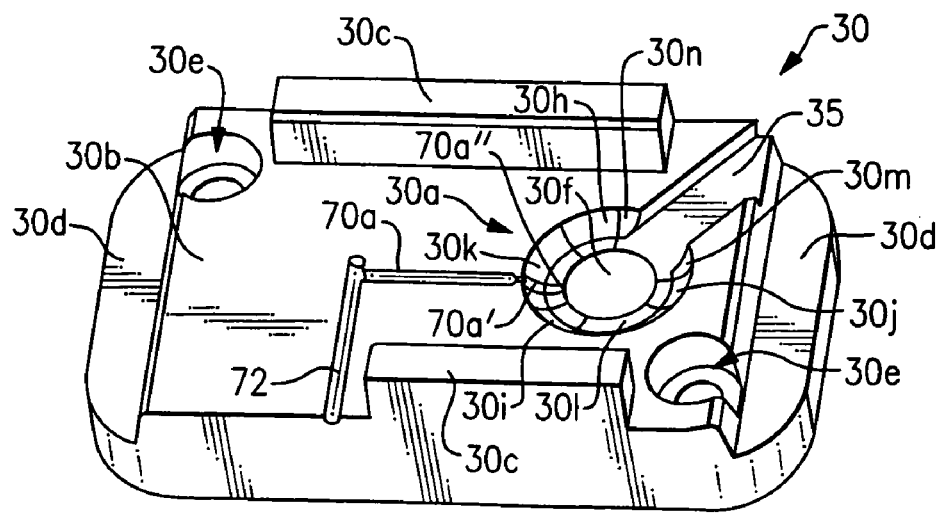
FIG. 3 is a perspective view of a second half of a cavity block according to an embodiment of the invention.

Referring now to the drawing, there is seen in FIG. 1 an embodiment of a dual optic accommodative intraocular lens device 10 which may be made with the present invention. Briefly, lens device 10 includes first and second optics 12, 14 interconnected by one or more, but preferably three, haptics 16a, 16b and 16c defining three open spaces 18a, 18b, 18c therebetween, respectively. Haptics 16a-c bow outwardly past the optic perimeters 12p, 14p and are flexible whereby the optics may move alternately toward and away from each other generally along the optical axis OA-OA. Optics 12, 14 and haptics 16a-c are formed as a unitary element and may be made of any suitable IOL liquid lens material such as silicone, for example. First optic 12 may be a double convex positive lens and second optic 14 may be a plano-concave negative lens positioned posterior relative to first optic 12 in an eye as described more fully in the Sarfarazi patents listed above.

Referring to FIGS. 2-6B, first and second cavity blocks 30, 32 are provided each having a cavity portion 30a, 32a which, when assembled in facing relation, form a completed cavity shaped to mold a lens device of the desired configuration therein. For purposes of description, cavity blocks 30, 32 will be described in the configuration for molding the dual optic lens device 10 shown in FIG. 1. Each cavity block includes a base 30b, 32b having one or more alignment features such as taper locks 30c, 32c and cut-outs 30d, 32d, respectively, which mate to properly align the cavity tool portions 30a, 30b when the cavity blocks are brought together. The cavity blocks 30, 32 are mounted with appropriate mounting pins into respective halves 80a, 80b of a mold base 80 (FIGS. 6A and 6B), particulars of which are explained more fully below. Mold base 80 is mounted in an injection mold machine (not shown) operable to alternately open and close the cavity blocks 30, 32 between molding cycles. The molding machine set-up of course provides all necessary mold processing apparatus such as, for example, electronic controls, heating elements for curing the lens device in the cavity, cooling elements, and an injection nozzle assembly for injecting the liquid lens material into the mold cavity.

Cavity tool portions 30a, 32a each include an optical surface 30f, 32f which form the outwardly facing surfaces 12a, 14a of lens optics 12, 14, respectively. The inwardly facing surfaces 12b, 14b of lens optics 12, 14 are formed by first and second optical surfaces 40a, 40b provided on mold insert 40 (FIGS. 4A-D), respectively. In the preferred embodiment, all mold optical surfaces are provided on individual inserts which are removably attached to their respective mountings. More particularly, as seen in FIGS. 5C and 5D, optical surfaces 30f, 32f are provided on respective tool inserts 50, 52 which are removably mounted through openings 30g, 32g in respective cavity blocks 30, 32, respectively. Backing plates 60, 62 abut cavity blocks 30, 32 and are secured thereto via bolts 60a, 62a having shanks 60b, 62b which thread into the non-optical ends 50a, 52a of optical inserts 50, 52, respectively. Optical surfaces 30f, 32f are preferably formed by EDM or diamond turned metal of high optical quality and thermal conductivity (e.g., CuNi).

The outwardly facing surfaces 16a'-c' of haptics 16a-c of lens device 10 are formed by cavity surfaces 30h,i,j in cavity portion 30a (FIG. 3), and by cavity surfaces 32h,i,j in cavity portion 32a (FIG. 2), respectively. Cavity surfaces 30h,i,j and 32h,i,j are recessed relative to intervening cavity surfaces 30k,l,m and 32k,l,m for reasons explained below. When optical inserts 50, 52 are mounted in cavity blocks 30, 32, the optical surfaces 30f, 32f thereof are located radially inward and adjacent cavity surfaces 30h,i,j and 32h,i,j, respectively. When cavity blocks 30, 32 are brought together, the parting line PL is preferably located about the midline of lens device 10 defined by a plane intersecting the haptics 16a-c at their largest outer diameter.

Figure 4A:
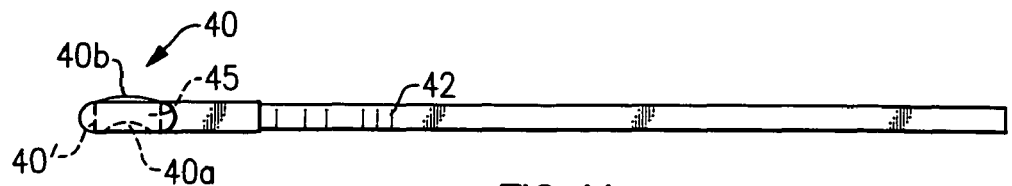
FIG. 4A is a side elevational view of an embodiment of the mold insert of the invention.
Figure 4B:
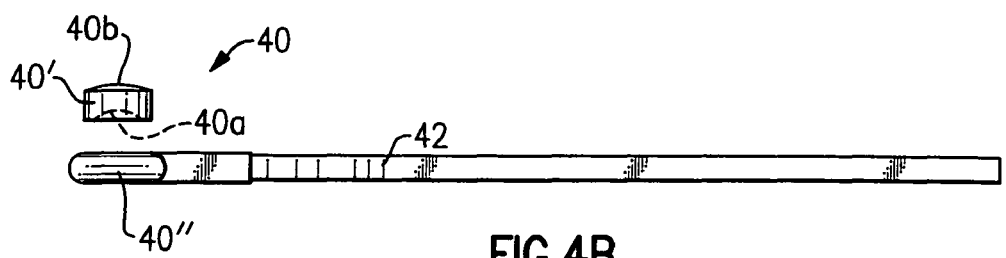
FIG. 4B is the view of FIG. 4A showing the optical insert in spaced relation to the other parts of the mold insert.
Figure 4C:
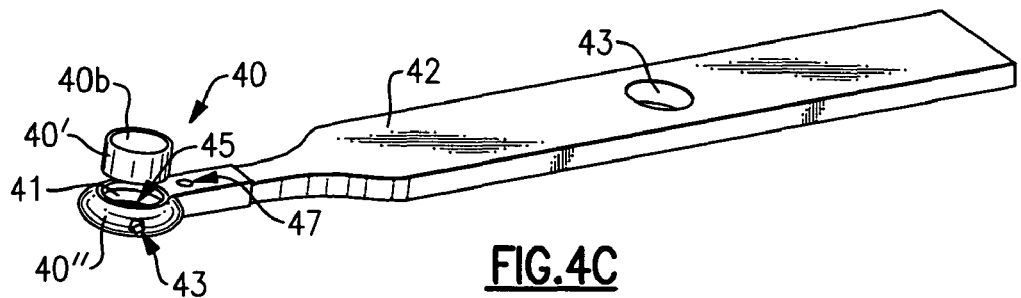
FIG. 4C is a perspective view of FIG. 4B.
Figure 4D:
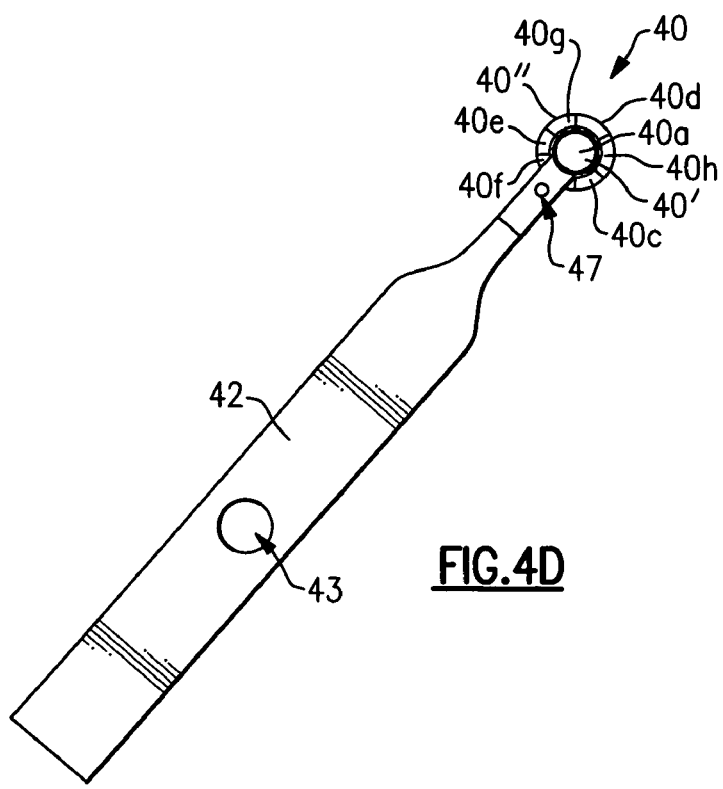
FIG. 4D is a plan view of FIG. 4A.
Figure 5A:
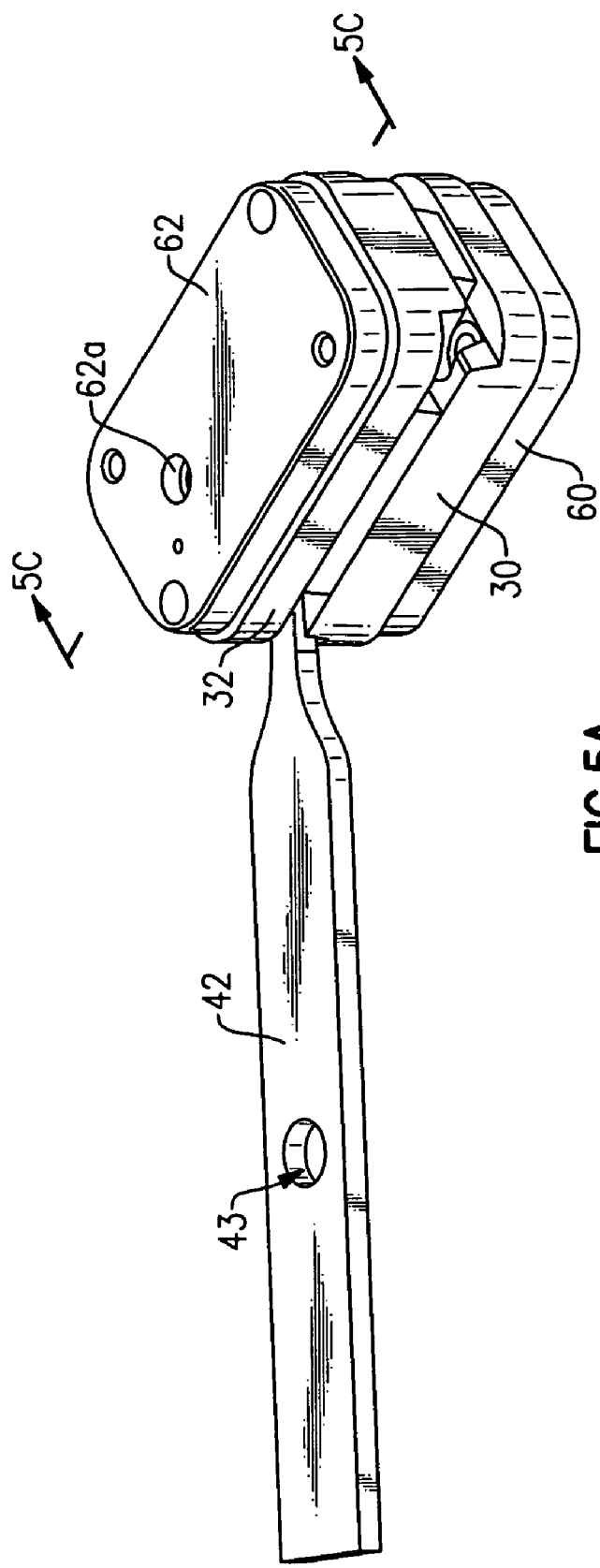
FIG. 5A is a perspective view of the cavity blocks and inserts in their assembled, closed condition.

The inwardly facing surfaces 16a"-c" of haptics 16a-c are formed by cavity surfaces 40c,d,e on annular portion 40" of mold insert 40 (FIG. 4D). The annular portion 40" is preferably of uniform thickness about its circumference and is sized such that haptic forming cavities $HC_{1-3}$ are created between mold insert surfaces 40c,d,e and cavity surfaces 30h,i,j and 32h,i,j (which are recessed relative to intervening cavity surfaces 30k,l,m and 32k,l,m) when the mold is closed as seen in FIGS. 5A-D. (Only one haptic cavity $HC_1$ is seen in FIGS. 5C and 5D.) Liquid lens material is prevented from flowing between the haptic forming cavities $HC_{1-3}$ due to the close, abutting relationship of mold insert surfaces 40f,g,h and cavity surfaces 30k,l,m and 32k,l,m. Since lens material cannot flow here, open spaces 18a,b,c are thereby created between haptics 16a,b,c in the molded lens device 10 (see FIG. 1).

In a preferred embodiment, mold insert 40 is attached to a handle 42 to assist in alternately inserting and removing mold insert 40 from between cavity blocks 30, 32. In this embodiment, the handle part resides between grooves 35, 37 provided in cavity blocks 30, 32, respectively, and cuts off mold flow to the area between haptic forming surfaces 30h,j and 32h,j. A hole 43 in handle 42 may be engaged with a pin 81 provided in the mold base 80 (see FIG. 6A) to align mold insert 40 between optical surfaces 30f, 32f In this embodiment, pin 81 is provided on core clamping plate 87 and extends through a hole 86a provided in core plate 86. The hole 86a is located in a linear recess 86b which is coextensive with recess 35 in cavity block 30 to accommodate mold insert handle 42 therein. Other alignment means may of course be used as desired.

As seen in FIGS. 4B,C, optical surfaces 40a,b are provided on an insert 40' that is mounted in the central opening 45 of annular mold insert surface 40". Insert 40' may be secured thereto by injecting a quantity of liquid adhesive through a hole 43 extending to a groove 41 provided on the inside diameter of mold insert annular portion 40" (FIG. 4C). By providing insert 40' and annular portion 40" as separate components, they may be made of different materials and have different surface finishes. For example, insert 40' which forms the device optics may be made of diamond turned metal while annular portion 40" which forms the device haptics may be made of a high quality, thermally resistant plastic material such as ALTEM that is capable of repeated molding cycles, or vice-versa. Other methods for securing insert 40' within opening 45 may of course be used (e.g., friction fit, mechanical interlock, etc.).

To begin a molding cycle, mold insert 40 is placed between cavity blocks 30,32 as described above. In a preferred embodiment, the mold insert 40 is laid upon one of the cavity blocks 30 or 32 first with handle 42 residing in the respective groove 35 or 37. The second cavity block is then moved against the first cavity block, sandwiching mold insert 40 therebetween and creating the mold cavity. When molding lens devices having concave and convex optical surfaces such as lens device 10, it is preferred that the concave optical surface 40a of mold insert 40 which is responsible for making the convex optical surface 12b of the lens device, is first placed face-down in cavity block 30. This is to reduce the chance of scratching the convex optical surface 40b of the mold insert which is face-up and not being brought to bear against a cavity block at this point. This is particularly true in the case where the mold insert 40 is being manually placed on the cavity block by a worker who may inadvertently touch a protruding convex surface 40b of the mold insert with parts of the cavity block when trying to place this side down in the cavity block. Should such scratching occur, this would transfer to the molded lens device which would have to be scrapped. By instead placing the concave surface 40a face down, there is less chance that the worker could inadvertently touch the concave surface 40a (since it is recessed) with parts of the cavity block against which it is being laid. In the embodiment of lens device 10, the cavity block 30 responsible for forming the positive optic 12 (double convex) is thus positioned below the cavity block 32 for forming the negative optic 14 (plano-concave) wherein mold insert 40 is first placed on cavity block 30 with mold insert concave surface 40a facing cavity surface 30a (see FIG. 6A). Cavity block 32 is then moved against cavity block 30 to create the mold cavity ready to receive liquid lens material (FIGS. 5A-D).

Figure 6A:
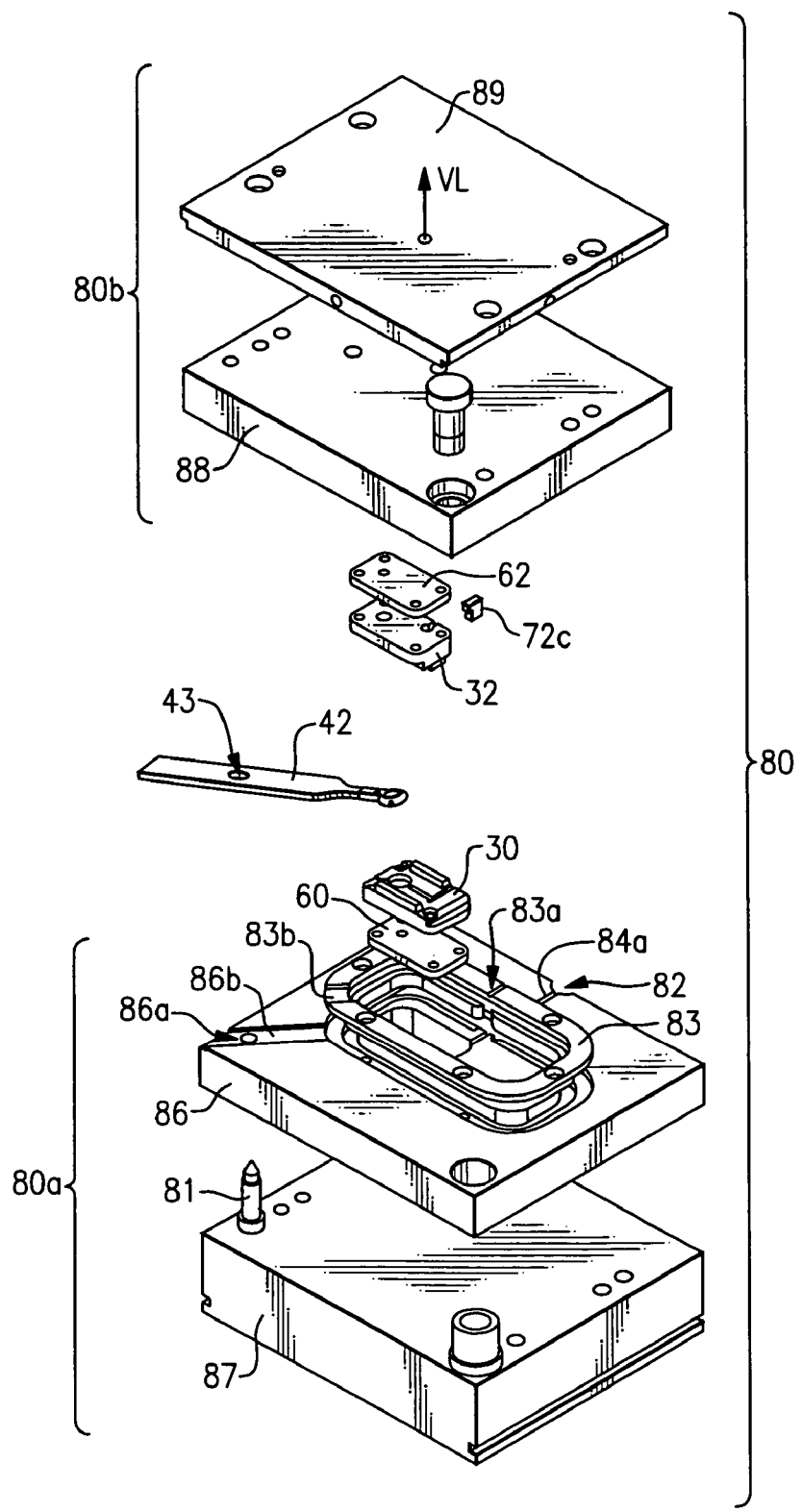
FIG. 6A is an exploded, perspective view of the mold base, cavity blocks and mold inserts.
Figure 6B:
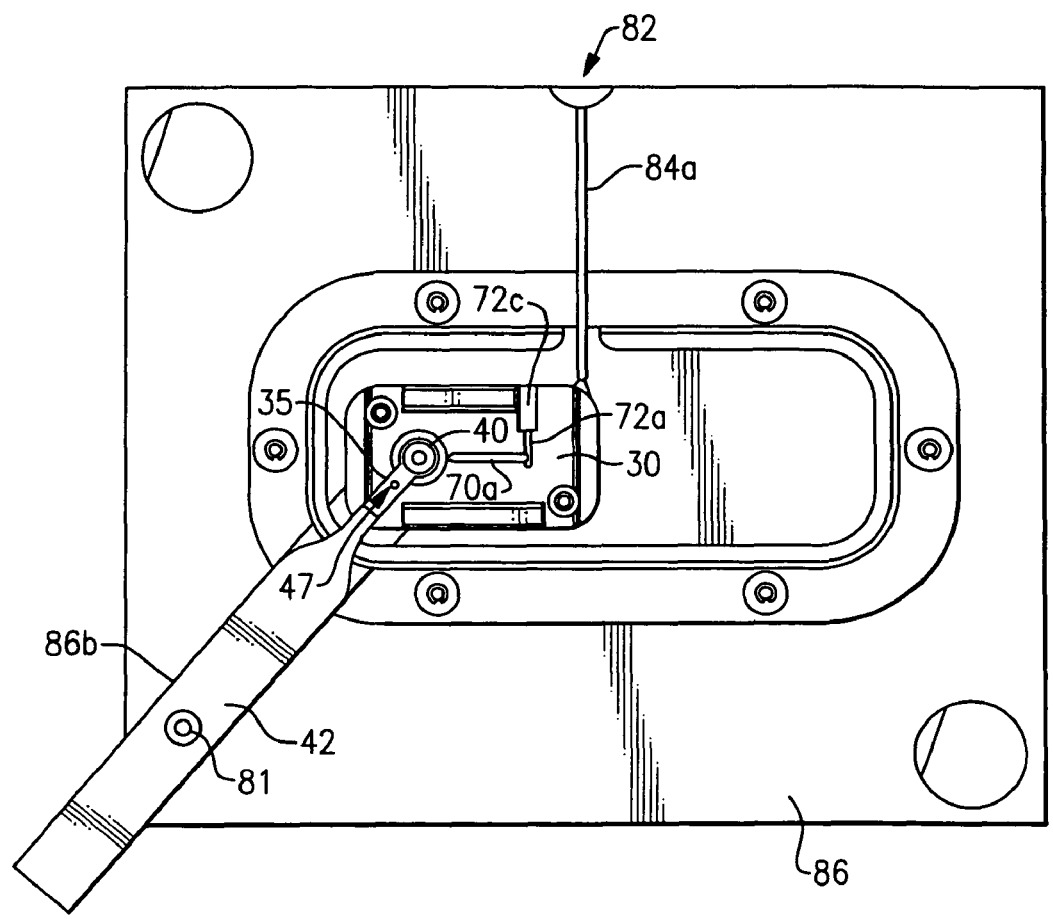
FIG. 6B is a plan view of one half of the mold base with the associated cavity block and mold insert.
Figure 6C:
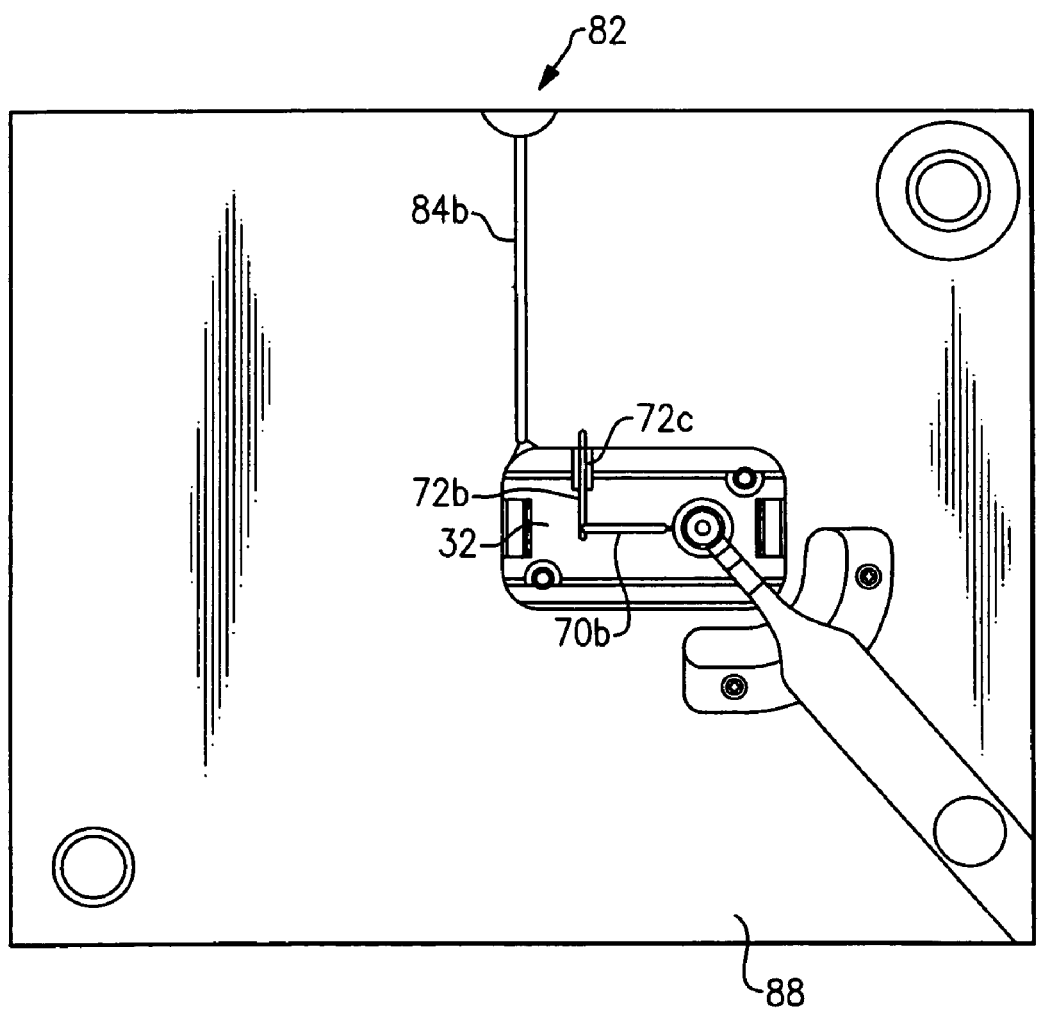
FIG. 6C is a plan view of the other half of the mold base with the associated cavity block and mold insert.
Figure 6D:
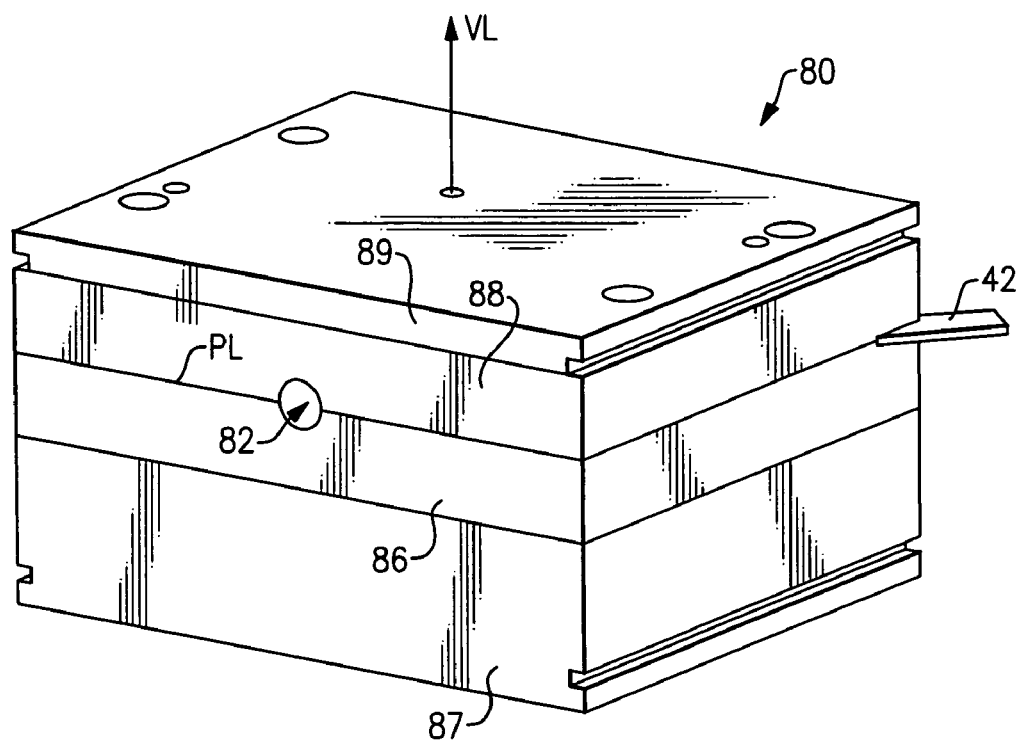
FIG. 6D is a perspective view of the assembled mold base.

Referring again to FIGS. 2, 3 and 5C,D and 6A-D, a preferably full-round primary runner 70 is formed by facing half-round runner surfaces 70a, 70b provided in cavity blocks 30, 32, respectively. Runner geometries other than round are of course possible. A cavity block runner 72, which may extend co-planar for a horizontal injection (as shown) or perpendicular for a vertical injection (not shown) to primary runner 70, is formed by runner surfaces 72a and 72b in cavity blocks 30, 32, respectively, when the mold is closed. The core plates 86, 88, in which cavity blocks 30, 32 are respectively mounted (FIGS. 6B, C), include runner halves 84a, 84b which, when the mold is closed, form lead-in runner 84 which extends into cavity block runner 72 which, in turn, extends into primary runner 70. A runner insert 72c provides a bridge between runner surface 72b and 84b in cavity block 32 (FIGS. 6B,D).

Primary runner 70 then extends toward the mold cavity and branches into first and second sub-runners 70a', 70b' which extend into the optical cavities $OC_1$ and $OC_2$ through first and second gates 70a", 70b" respectively. The first and second gates 70a" and 70b" are preferably located at the perimeter of the optical cavities $OC_1$ and $OC_2$ between adjacent haptic-forming cavities. In this regard, it is noted that the sub-runners 70a', 70b' are formed in part by the annular portion 40" of mold insert 40 (refer to the inner arcs of the sub-runners in cross-sectional view of FIGS. 5C, D). The general locations of first and second gates 70a" and 70b" are indicated with respect to the finished lens in FIG. 1. The first and second gates 70a", 70b" are preferably configured to taper inwardly into their respective mold cavities $OC_1$, $OC_2$ such that little or no gate vestige is created at these areas of the molded lens device. In a preferred embodiment, the gates 70a", 70b" taper at an angle of between about 5 and 25 degrees, more preferably between about 10 and 20 degrees, and most preferably taper at an angle of about 15 degrees. The taper length is preferably about 0.1 to 1.0 mm and more preferably is about 0.53 mm.

Referring particularly to FIGS. 5 and 6, liquid lens material (e.g. silicone) is injected through inject port 82, through lead-in runner 84, through cavity block runner 72, through primary runner 70, then branching through both the first and second sub-runners 70a', 70b'. The diameters of sub-runners 70a', 70b' are preferably substantially equal such that substantially equal amounts of liquid lens material travels therethrough although this may change depending on the lens design. This creates two flow fronts which meet at about the midline of the haptic cavities $HC_{1-3}$. This is preferable over a flow front that meets at one or both of the optical cavities $OC_1$ and $OC_2$ since unacceptable optics could result. To enhance material flow, the diameters of the runners may step down toward the cavity. In liquid injection molding, the material is injected at a cool temperature relative to the heated mold cavity. In the present embodiment, liquid silicone is injected at a temperature of about 30° F. to 50° F. and more preferably at about 40° F.

Once the liquid lens material has been injected, heat is applied to the mold base 80 to cure the liquid lens material (e.g., in the range of about 250° F. to 300° F. and more preferably about 280° F.). In a preferred embodiment, a vacuum may be drawn from the mold cavity through vacuum line VL to assist in the injection of the liquid lens material. Application of a vacuum during injection may be desirable to eliminate air bubbles and ensure a complete fill of the mold cavities. The vacuum may also help reduce flash. A hole 47 is provided in mold insert handle 42 where the vacuum line begins. A gasket 83 may be applied in surrounding relation to the cavity blocks 30,32 to help create an air-tight seal for a more effective vacuum draw. The gasket may have a runner groove 83a which aligns with the lead-in runner half 84a, as well as a groove 83b which aligns with groove 86b to accommodate the mold insert handle 42.

Figure 4E:
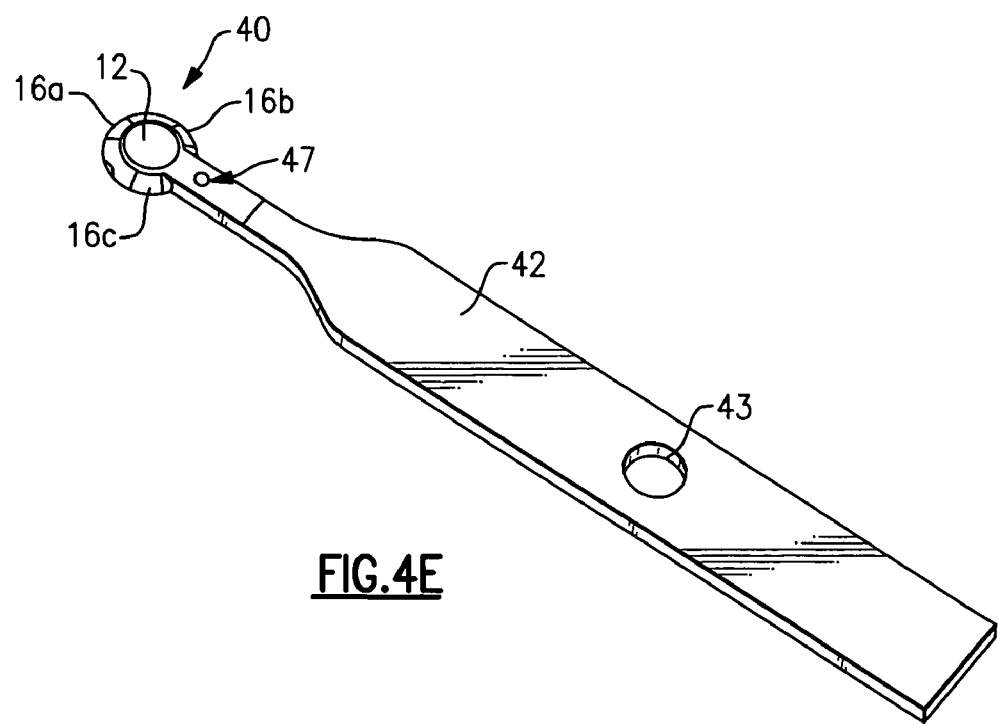
FIG. 4E is a perspective view of the mold insert with a molded IOL attached thereto.

Once the lens material has cured, the cavity blocks are cooled to permit opening of mold base halves 80a, 80b along parting line PL. Mold insert 40 is removed from between cavity blocks 30, 32 using handle 42. Lens device 10 remains adhered about mold insert 40 at this point (FIG. 4E). Due to the tapered gate configuration, the liquid lens material in the runners should remain with one of the cavity blocks and have a clean break from the lens device 10. Should they remain attached to the lens device 10, they may be carefully removed therefrom. To remove the lens device 10 from mold insert 40, two of the haptics 16a-c (preferably the two on either side of handle 42) are carefully stretched apart to permit the passage of mold insert 40 therebetween. Due to the resilient nature of the liquid lens material, the lens device 10 quickly returns to its unstretched state.

As stated above, different surface finishes may be applied to one or more preselected cavity surfaces to provide different surface characteristics to different portions of the molded lens device 10 as desired. A different surface finish may be desirable on the outwardly facing surfaces of haptics 16a-c to improve visualization thereof during implantation. For example, a "frosted" haptic appearance may be created by making the haptic forming mold cavity surfaces with an Ra of between about 0.15μ to 1.25μ, and more preferably between about 0.3μ and 0.75μ and most preferably about 0.55μ.

Surface finishes may also be used to ease the removal of the lens device from the mold insert 40. Since mold device 10 may be formed of a flexible material such as silicone, it may be removed from insert 40 by carefully stretching the haptics such that the mold insert may pass through the space defined between adjacent haptics as described above. A surface finish which is too smooth is undesirable since silicone will have a tendency to stick to a very smooth surface creating difficulty in release from the cavity and the paddle. On the other hand, a surface finish that is too rough will impart unacceptable imperfections to the lens. The surface finish should therefore be somewhere between very smooth and very rough. An Ra surface finish of between about less than or equal to 15 nm has been found to produce acceptable lens release and lens surface quality. Surface finishes may be determined using any type of known method and machine, e.g., a Zygo Newview microscope at 10×.

What is claimed is:

1. Apparatus for injection molding an intraocular lens having first and second optics, said apparatus comprising:
   a) a first optic cavity for forming said first optic;
   b) a second optic cavity for forming said second optic;
   c) a first sub-runner in fluid communication with said first optic cavity;
   d) a second sub-runner in fluid communication with said second optic cavity; and
   e) one or more haptic cavities extending between and in fluid communication with said first and second optic cavities, said one or more haptic cavities configured to form one or more haptics extending between and interconnecting said first and second optics, respectively.

2. The apparatus of claim 1, and further comprising a primary runner from which said first and second sub-runners branch off and extend to said first and second optic cavities, respectively.

3. The apparatus of claim 1 wherein said first and second sub-runners have a substantially circular cross-section.

4. The apparatus of claim 3 wherein said primary runner has a substantially circular cross-section.

5. The apparatus of claim 1 and further comprising a mold insert having first and second optical surfaces defining in part said first and second optic cavities, respectively.

6. The apparatus of claim 5 and further comprising a handle to which said mold insert is attached whereby said handle may be used for alternately locating and removing said mold insert from said apparatus between molding cycles.

7. The apparatus of claim 5 and further comprising first and second cavity blocks each having an optical surface, said optical surface of said first and second cavity blocks and said first and second optical surfaces of said mold insert together defining said first and second optical cavities, respectively.

8. The apparatus of claim 1 wherein said first and second sub-runners extend substantially horizontally.

9. The apparatus of claim 8 wherein said primary runner extends substantially horizontally.

10. The apparatus of claim 1 wherein first and second injection gates are defined at a juncture of said first optic cavity and said first sub-runner, and at a juncture of said second optic cavity and said second sub-runner, respectively, said first and second injection gates each tapering inwardly into said first and second optic cavities, respectively.

11. The apparatus of claim 10 wherein said taper is between about 5 and 25 degrees.

12. The apparatus of claim 10 wherein said taper is between about 10 and 20 degrees.

13. The apparatus of claim 10 wherein said taper is about 15 degrees.

14. The apparatus of claim 1 wherein said first optic cavity is shaped to form a positive lens, and said second optic cavity is shaped to form a negative lens.

15. The apparatus of claim 14 wherein said first optic cavity is positioned below said second optic cavity.

16. The apparatus of claim 15 and further comprising a mold insert having first and second optic surfaces defining in part said first and second mold cavities, respectively.

17. The apparatus of claim 16 and further comprising a handle to which said mold insert is attached whereby said handle may be used for alternately locating and removing said mold insert from said apparatus between molding cycles.

18. The apparatus of claim 1 wherein said first and second optic cavities are formed in part by first and second optical surfaces defined on first and second tool inserts, respectively.

19. The apparatus of claim 18 and further comprising first and second cavity blocks wherein said first and second tool inserts are removably mounted, respectively.

20. The apparatus of claim 19 and further comprising a mold insert having first and second optical surfaces which, together with said first and second optical surfaces of said first and second tool inserts, define said first and second optic cavities, respectively.

21. The apparatus of claim 20 wherein said mold insert is removably mounted between said first and second cavity blocks.

22. The apparatus of claim 19 and further comprising at least one haptic forming cavity formed between said first and second cavity blocks radially outwardly of said first and second optical surfaces.

23. The apparatus of claim 22 and further comprising a mold insert having first and second optical surfaces which, together with said first and second optical surfaces of said first and second tool inserts, define said first and second optic cavities, respectively.

24. The apparatus of claim 23 wherein said haptic forming cavity is defined at least in part by said mold insert.

25. The apparatus of claim 23 wherein said mold insert includes an annular surface which defines at least part of said haptic forming cavity.

26. The apparatus of claim 25 wherein said first and second optical surfaces of said mold insert are formed on a tool insert circumscribed by said annular surface.

27. The apparatus of claim 26 wherein said tool insert of said mold insert is adhesively secured to said annular surface.

28. The apparatus of claim 27 wherein said annular surface includes a through hole wherethrough adhesive may be injected to secure said mold insert to said annular surface.

29. The apparatus of claim 28 and further comprising a handle attached to said mold insert.

30. The apparatus of claim 29 and further comprising first and second grooves formed in said first and second cavity blocks wherein said handle resides when said first and second cavity blocks are placed in abutting relation.

* * * * *